United States Patent
Reinhardt

(10) Patent No.: US 8,758,609 B2
(45) Date of Patent: Jun. 24, 2014

(54) FITTING COUPLER FOR PLANAR FLUID CONDUIT

(75) Inventor: Thomas Reinhardt, Karlsruhe (DE)

(73) Assignee: Agilent Technologies, Santa Clara, CA (US)

( * ) Notice: Subject to any disclaimer, the term of this patent is extended or adjusted under 35 U.S.C. 154(b) by 159 days.

(21) Appl. No.: 13/195,077

(22) Filed: Aug. 1, 2011

(65) Prior Publication Data

US 2012/0031820 A1   Feb. 9, 2012

(30) Foreign Application Priority Data

Aug. 3, 2010 (GB) .................................. 1012992.2

(51) Int. Cl.
*B01D 15/10* (2006.01)
*B01D 35/30* (2006.01)
*F16L 37/05* (2006.01)
*G01N 30/00* (2006.01)
*F16L 19/00* (2006.01)

(52) U.S. Cl.
USPC ........ 210/198.2; 210/459; 210/460; 210/232; 73/61.56; 137/798; 285/382

(58) Field of Classification Search
None
See application file for complete search history.

(56) References Cited

U.S. PATENT DOCUMENTS

| 4,883,409 | A | 11/1989 | Strohmeier et al. |
| 4,982,597 | A | 1/1991 | Berger |
| 5,074,599 | A | 12/1991 | Wirbel et al. |
| 6,361,687 | B1 * | 3/2002 | Ford et al. .................. 210/198.2 |
| 6,827,095 | B2 | 12/2004 | O'Connor et al. |
| 2008/0142479 | A1 | 6/2008 | Beerling et al. |

FOREIGN PATENT DOCUMENTS

| EP | 0309596 A1 | 4/1989 |
| WO | 2009121410 A1 | 10/2009 |
| WO | 2010000324 A1 | 1/2010 |

* cited by examiner

*Primary Examiner* — Benjamin Kurtz

(57) ABSTRACT

A fitting coupler is provided configured for coupling a planar fluid conduit and a fluidic device. The fluidic device comprises a cavity, a device conduit, and a mouth where the device conduit opens into the cavity. A contact pressure element is configured for sealingly pressing the planar fluid conduit to the mouth, so that a conduit opening of the planar fluid conduit opens into the mouth.

14 Claims, 7 Drawing Sheets

FITTING COUPLER FOR PLANAR FLUID CONDUIT

This application claims priority from United Kingdom Patent Application No. GB 2010129922 filed on 3 Aug. 2010, which is incorporated by reference in its entirety.

The present invention relates to coupling a planar fluid conduit to a fluidic device, in particular in a high performance liquid chromatography application.

BACKGROUND

In high performance liquid chromatography, a liquid has to be provided usually at a very controlled flow rate and at high pressure at which compressibility of the liquid becomes noticeable. For liquid separation in an HPLC system, a mobile phase comprising a sample fluid with compounds to be separated is driven through a stationary phase, thus separating different compounds of the sample fluid which may then be identified.

The mobile phase, for example a solvent, is pumped under high pressure typically through a column of packing medium, and the sample to be analyzed is injected into the column. As the sample passes through the column with the liquid, the different compounds, each one having a different affinity for the packing medium, move through the column at different speeds. Those compounds having greater affinity for the packing medium move more slowly through the column than those having less affinity, and this speed differential results in the compounds being separated from one another as they pass through the column.

The mobile phase with the separated compounds exits the column and passes through a detector, which identifies the molecules, for example by spectrophotometric absorbance measurements. A two-dimensional plot of the detector measurements against elution time or volume, known as a chromatogram, may be made, and from the chromatogram the compounds may be identified. For each compound, the chromatogram displays a separate curve or "peak". Effective separation of the compounds by the column is advantageous because it provides for measurements yielding well defined peaks having sharp maxima inflection points and narrow base widths, allowing excellent resolution and reliable identification of the mixture constituents. Broad peaks, caused by poor column performance, so called "Internal Band Broadening" or poor system performance, so called "External Band Broadening" are undesirable as they may allow minor components of the mixture to be masked by major components and go unidentified.

An HPLC column typically comprises a stainless steel tube having a bore containing a packing medium comprising, for example, silane derivatized silica spheres having a diameter between 0.5 to 50 µm, or 1-10 µm or even 1-7 µm. The medium is packed under pressure in highly uniform layers which ensure a uniform flow of the transport liquid and the sample through the column to promote effective separation of the sample constituents. The packing medium is contained within the bore by porous plugs, known as "frits", positioned at opposite ends of the tube. The porous frits allow the transport liquid and the chemical sample to pass while retaining the packing medium within the bore. After being filled, the column may be coupled or connected to other elements by e.g. using fitting elements. Such fitting elements may contain porous parts such as screens or frit elements.

During operation, a flow of the mobile phase traverses the column filled with the stationary phase, and due to the physical interaction between the mobile and the stationary phase a separation of different compounds or components may be achieved. In case the mobile phase contains the sample fluid, the separation characteristics is usually adapted in order to separate compounds of such sample fluid. The term compound, as used herein, shall cover compounds which might comprise one or more different components. The stationary phase is subject to a mechanical force generated in particular by a hydraulic pump that pumps the mobile phase usually from an upstream connection of the column to a downstream connection of the column. As a result of flow, depending on the physical properties of the stationary phase and the mobile phase, a relatively high pressure occurs across the column.

Fittings for coupling different components, such as separation columns and conduits, of fluidic devices are commercially available and are offered, for instance, by the company Swagelok. A typical tube fitting is disclosed in U.S. Pat. No. 5,074,599 A.

WO 2010/000324 A1, by the same applicant, discloses a fitting for coupling a fluid conduit to another component of a fluidic device.

U.S. Pat. No. 6,827,095 B2 discloses modular microfluidic systems with planar couplers coupled between. Planar couples from micro-machined titanium for high pressure microfluidic applications are disclosed by the same applicant in US 2008/0142479 A1.

WO 2009/121410 A1, by the same applicant, discloses planar fluidic conduits and the coupling thereof to other devices.

SUMMARY

It is an object of the invention to provide an improved coupling of planar fluid conduit to a fluidic device, in particular to standard fitting interfaces as applied in HPLC applications. The object is solved by the independent claim(s). Further embodiments are shown by the dependent claim(s).

According to embodiments of the present invention, a fitting coupler is provided and configured for coupling a planar fluid conduit to a fluidic device. The fluidic device comprises a cavity and further has a mouth into the cavity. The fitting coupling comprises a contact pressure element, which is configured for sealingly pressing a conduit opening of the planar fluid conduit to the mouth. Thus, a direct fluidic coupling between the planar fluid conduit and the device conduit can be achieved, which allows reducing dead volume and other unwanted effects when coupling fluidic conduits, such as cross contamination. Such embodiments are in particular useful when the cavity of the fluidic device is embodied to interact with standard fittings as mentioned in the introductory part of the description. Such standard fitting receiving cavities provide standard interfaces, which however are designed to couple circular shaped conduits, such as capillaries. Embodiments of the invention allow using such standard fitting receiving cavities also for coupling planar fluid conduits, which is in particular useful in low volume flow applications, for example, with flow rates from typically 100 to 500 nl/min or less. Such flow rates are used in Nano-LC coupled to MS. Applications which are more standard of today are using flow rates in the range of 1 to 100 µl/min for Capillary-LC or more up to ml/min.

In one embodiment, the fitting coupler further comprises a guidance configured for receiving the planar fluid conduit and for guiding the planar fluid conduit into the cavity. This allows securely introducing the planar fluid conduit into the cavity and guiding it to provide the fluidic coupling to the fluidic device. Such guidance may be or comprise a through-hole and might either loosely or securely hold the planar fluid conduit in position. The guidance may also be designed to prevent rotation of the sealing surface while the connection is tightened. Pressure in combination with rotation onto the sealing surface may lead to failure or leak, because the sealing device or surface can be destroyed under such sealing pressures as required to withstand e.g. several 100 bar or more. The guidance may also be comprised as a part of a screw or an assembly.

In one embodiment, the fitting coupler may comprise one or more of the following. The contact pressure element may comprise an axial force element configured to exert an axial force in an axial direction with respect to the cavity, e.g. with respect to an elongation of the cavity. The axial force element thus provides a pressing force to sealingly press the conduit opening to the mouth. By adequately designing the axial force element, the sealing properties can be adjusted and configured for the respective application as well as the specific characteristic of the abutting elements, in particular the planar fluid conduit and the fluidic device. The axial force element may comprise a thread element configured to act together with a device thread element of the fluidic device to exert the axial force. The axial force element may be configured to exert the axial force as a spring-biased force, thus allowing accommodating for tolerances or variations during use, e.g. under changing thermal conditions. The fitting coupler parts are preferably designed to endure such changing conditions without relaxing the contact pressure of the sealing surface. This can be achieved e.g. with elements acting in an elastic range without being overloaded into the ductile range.

In one embodiment, the contact pressure element is configured for interacting with the cavity to sealingly press the conduit opening of the planar fluid conduit to the mouth. For example, the contact pressure element may be configured to interact with a surface of the cavity for sealingly pressing the conduit opening to the mouth.

In one embodiment, the fitting coupler comprises a front face configured to abut against a contact side of the device conduit having the device opening. In one embodiment, the planar fluid conduit is guided along a lateral side of the front face and bent over the front face, so that in use the end side of the planar fluid conduit is interposed between the front face of the fitting coupler and the contact side of the device conduit.

In one embodiment, the fitting coupler comprises a front element and a rear element. The front element comprises the front face. A rear side of the front element is located at a side opposite to the front face. The rear element is configured to abut against the rear side of the front element and to exert an axial force on the front element in an axial direction with respect to the cavity. The front element and the rear element may be embodied as two individual parts but integrally coupled with each other, or the front element and the rear element may be configured to be detachable or removable from each other. One of the front element and the rear element may be configured to be rotatable with respect to the other and also with respect to the fluidic device. For example, the rear element may be configured to be rotatable with respect to the front element as well as with respect to the fluidic device. Such embodiments may allow decoupling movement of one of the front element and the rear element from each other, so that, for example the rear element can be rotated while the front element is not rotated but substantially stays in its position. This can allow that the rotational movement is translated into the axial force, for example by providing a thread mechanism as well known in the art. Preferably, the non-rotating part of the front and rear elements is configured to receive and guide the planar fluid conduit, so that the planar fluid conduit remains in its position when the other component is rotated but experiences the axial force to sealing decouple with the fluidic device.

In one embodiment, the rear element is configured to decouple the planar fluid conduit from a rotational movement of the rear element. The rear element may comprise a thread element configured to act together with a device thread element of the fluidic device to exert a force on the rear side of the front element.

In one embodiment, the planar fluid conduit is part of the fitting coupler. The planar fluid conduit has a conduit channel with an essentially planar shape. The conduit opening at the end of the planar fluid conduit is in fluidic communication with the conduit channel. The planar fluid conduit may extend to a front face of the fitting coupler and abut against a contact side of the device conduit having the device opening.

In one embodiment, the contact pressure element is configured to press the planar fluid conduit against the device, so that the conduit opening of the planar fluid conduit sealingly couples to the device opening of the device conduit.

In one embodiment of the present invention, a planar fluid conduit is provided, which comprises a conduit channel with an essentially planar shape, and a conduit opening at an end of the planar fluid conduit which is in fluidic communication with the conduit channel. The planar fluid conduit further comprises a fitting coupler which may be embodied in accordance with any of the aforementioned embodiments. The fitting coupler is coupled to the end of the planar fluid conduit and is configured for coupling the conduit opening to a mouth in a cavity of the fluidic device.

In one embodiment, a fitting is provided which comprises a fluidic device having a cavity and a mouth into the cavity. The fitting further comprises a planar fluid conduit having a conduit channel with an essentially planar shape, and a conduit opening at an end of the planar fluid conduit which is in fluidic communication with the conduit channel. The fitting further comprises a fitting coupler which may be in accordance to any of the aforementioned embodiments. The fitting coupler is coupled to the end of the planar fluid conduit and configured for coupling the conduit opening of the planar fluid conduit to the mouth.

The terms "fitting" and "fitting element", as used herein, shall both relate to coupling a fluid conduit to a fluidic device. The term "fitting" shall cover all components required for coupling the fluid conduit to the fluidic device, and may even comprise the fluid conduit and/or the fluidic device, or parts thereof. The term "fitting element" shall cover a part of the fitting.

The terms "axial" and "radial", as used herein, shall not be limited to circular embodiments of the fluid conduit only but shall cover any kind of shaping of the fluid conduit including rectangular fluid conduits such as in planar structures. The term "axial" shall be interpreted as being in a direction of the elongation of the fluid conduit, which typically also represents the direction of fluid flow in the fluid conduit. Accordingly, the term "radial" shall be interpreted as being in a direction of the lateral dimension of the fluid conduit and being essentially perpendicular to the direction of the elongation of the fluid conduit. Though most embodiments are described herein with respect to circular type of fluid conduits, it goes without saying that they can be adapted accordingly to any other shaping, in particular rectangular fluid conduits.

The term "fluidic device" as used herein may cover or refer to a fluid conduit or an apparatus such as an HPLC device, a fluid separation device, a fluid handling device, and/or a measurement device in general. Accordingly, embodiments of the invention cover couplings between individual fluid conduits as well as couplings between a fluid conduit and a device/apparatus.

The fluidic device may comprise a processing element configured for interacting with a sample fluid. The fluidic device may be configured to conduct a sample fluid through the fluidic device, a fluid separation system for separating compounds of a sample fluid, a fluid purification system for purifying a sample fluid, and/or to analyze at least one physical, chemical and/or biological parameter of at least one compound of a sample fluid.

According to embodiments of the present invention, a fitting element is provided, in particular for an HPLC application. The fitting element is configured for providing a fluidic coupling of a fluid conduit to a fluidic device. The fitting element comprises a gripping piece configured to exert a grip force between the fitting element and the fluid conduit, when the fluid conduit is coupled to the fluidic device. The gripping piece promotes the grip force to mechanically connect the gripping element with the fluid conduit, when the fluid conduit is coupled to the fluidic device. The fitting element further comprises a first housing element and a second housing element. Each housing element is configured as an individual component with respect to the other. Both, the first housing element and the second housing element, are configured to at least partly house the gripping piece, in particular the grip force distributor. At least one of the first housing element and the second housing element comprises a coupling element, which is configured to couple the first housing element and the second housing element, when the fluid conduit is decoupled from the fluidic device and the second housing element is moved in axial direction with respect to the fluid conduit. The coupling element can thus allow that the first housing element is held by the second housing element, when the second housing element is removed. This can ensure that the first housing element will not stick with either one of the fluid conduit or fluidic device, when opening the fitting element and separating the fluid conduit from the fluidic device, so that the first housing element can be removed from the fluidic device.

An embodiment of the present invention comprises a fluid separation system configured for separating compounds of a sample fluid in a mobile phase. The fluid separation system comprises a mobile phase drive, such as a pumping system, configured to drive the mobile phase through the fluid separation system. A separation unit, which can be a chromatographic column, is provided for separating compounds of the sample fluid in the mobile phase. The fluid separation system further comprises a fitting element and/or fitting as disclosed in any of the aforementioned embodiments for coupling a fluid conduit to a fluidic device in such fluid separation system. The fluid separation system may further comprise a sample injector configured to introduce the sample fluid into the mobile phase, a detector configured to detect separated compounds of the sample fluid, a collector configured to collect separated compounds of the sample fluid, a data processing unit configured to process data received from the fluid separation system, and/or a degassing apparatus for degassing the mobile phase. The fluidic device to which the fluid conduit is or can be coupled can be any of such devices, and plural of such fittings or fitting elements may be used within such fluid separation system.

Embodiments of the present invention might be embodied based on most conventionally available HPLC systems, such as the Agilent 1290 Series Infinity system, Agilent 1200 Series Rapid Resolution LC system, or the Agilent 1100 HPLC series.

One embodiment comprises a pumping apparatus having a piston for reciprocation in a pump working chamber to compress liquid in the pump working chamber to a high pressure at which compressibility of the liquid becomes noticeable. One embodiment comprises two pumping apparatuses coupled either in a serial or parallel manner, as disclosed e.g. in EP 309596 A1.

The mobile phase can be either a pure solvent or a mixture of different solvents. It can be chosen e.g. to minimize the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic is delivered in separate bottles, from which the gradient pump delivers a programmed blend to the system. Other commonly used solvents may be isopropanol, THF, hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The fluid is preferably a liquid but may also be or comprise a gas and/or a supercritical fluid.

The pressure in the mobile phase might range from 2-200 MPa, in particular 10-150 MPa, and more particular 50-120 MPa.

The HPLC system might further comprise a sampling unit for introducing the sample fluid into the mobile phase stream, a detector for detecting separated compounds of the sample fluid, a fractionating unit for outputting separated compounds of the sample fluid, or any combination thereof. Further details of HPLC system are disclosed with respect to the aforementioned Agilent HPLC series, provided by the applicant Agilent Technologies, under www.agilent.com which shall be in cooperated herein by reference.

BRIEF DESCRIPTION OF THE DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s). The illustration in the drawing is schematically.

DETAILED DESCRIPTION

Figure 1:
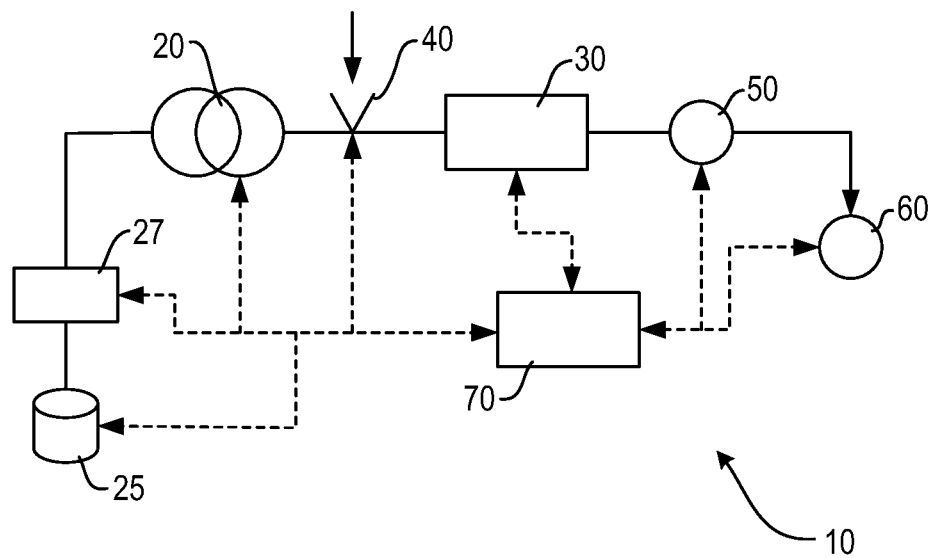
FIG. 1 shows in schematic view a liquid separation system 10, in accordance with embodiments of the present invention, e.g. used in high performance liquid chromatography.

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 comprising a stationary phase. A sampling unit 40 can be provided between the pump 20 and the separating device 30 in order to subject or add a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase occurs at high pressure and downstream of the pump 20. The composition of the mobile phase may be kept constant over time, the so called isocratic mode, or varied over time, the so called gradient mode.

A data processing unit 70, which can be a conventional PC or workstation, might be coupled to one or more of the devices in the liquid separation system 10 in order to receive information and/or control operation. For example, the data processing unit 70 might control operation of the pump 20 and receive therefrom information regarding the actual working conditions. The data processing unit 70 might also control operation of the solvent supply 25 and/or the degasser 27 and might receive therefrom information regarding the actual working conditions. The data processing unit 70 might further control operation of the sampling unit 40. The separating device 30 might also be controlled by the data processing unit 70, and send—in return—information to the data processing unit 70. Accordingly, the detector 50 might be controlled by the data processing unit 70, and send information to the data processing unit 70. The data processing unit 70 might also control operation of the fractionating unit 60 and provides data back.

For transporting liquid within the liquid separation system 10, typically fluid conduits are used as conduits for conducting the liquid. Fittings are commonly used to couple plural fluid conduits with each other or for coupling a fluid conduit to any device. For example, fittings can be used to connect respective fluid conduits to an inlet and an outlet of the chromatographic column 30 in a liquid-sealed fashion. Any of the components in the fluid path in FIG. 1 may be connected by fluid conduits using fittings. While the fluid path after the column 30 is usually at low pressure, e.g. 50 bar or below, the fluid path from the pump 20 to the inlet of the column 30 is under high pressure, currently up to 1200 bar, thus posing high requirements to fluid tight connections. The shape of the fluidic connection can be critical to applications. If the diameter of an e.g. 25 um inner diameter capillary suddenly opens to 100 um or more, this can be of a great disadvantage and jeopardize a good chromatographic result. One effect can be peak tailing or increased carry-over.

While tubular type fluid conduits are used in many conventional HPLC applications, the embodiments as disclosed in the following relate to planar fluid conduits. Such planar fluidic conduits are known in the art as described in the introductory part of the description and are often used in low volume flow applications such as applications requiring flow rates e.g. of 300 nl/min or less at column pressures of up to 1200 bar or more using fluid connections described above. Such planar fluid conduits might be used exclusively or only in addition, for example, in such HPLC system as schematically represented in FIG. 1.

The embodiments as disclosed in the following relate to the coupling of such planar fluid conduits to specific receiving cavities of any kind of device, which might be standard type receiving cavities for receiving standard fitting elements as readily known in the art and also described in the introductory part of the description. However, while such standard type fittings are commonly used for coupling tubular type conduits, such as capillaries with essentially round or elliptical cross section, and with the end of the respective fluid channel opening in axial direction of such tubular conduit, the following embodiments relate to planar fluid conduits having its opening at a lateral side of the conduit or, in other words, in a radial direction with respect to an axial elongation of the fluid path in the planar fluid conduit.

Figure 2:
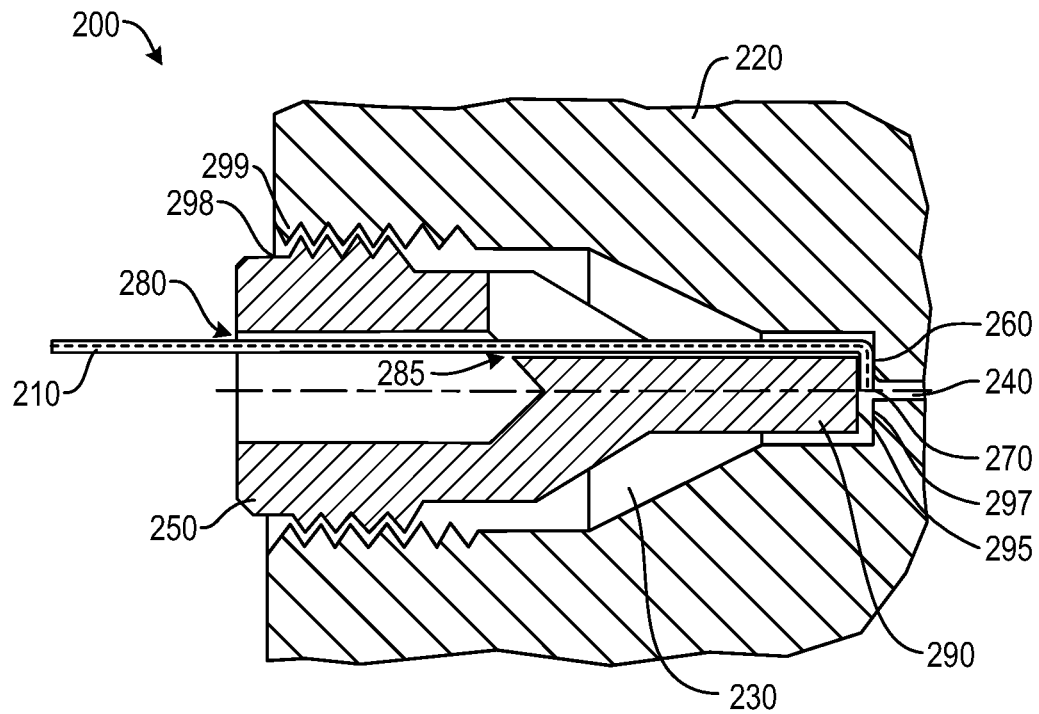
FIG. 2 illustrates a first embodiment of a fitting coupler 200 for coupling a planar fluid conduit 210 to a fluidic device 220.

FIG. 2 illustrates a first embodiment of a fitting coupler 200 for coupling a planar fluid conduit 210 to a fluidic device 220. As said, the fluidic device 220 might be any of the devices depicted in FIG. 1. The fluidic device 220, which is shown here only in a partial and cross sectional view, comprises a cavity 230 and a device conduit 240, which opens into the cavity 230. The shape of this cavity may be of standard shape as provided by the applicant or other vendors of capillaries and fitting systems. Typically the diameter of the receiving port is for capillary connections of about 1.6 mm or about 0.8 mm. In operation, the fitting coupler 200 provides a coupling between the planar fluid conduit 210 and the device conduit 240, so that a fluid flow path within the planar fluid conduit 210 opens into and is in fluidic communication with a fluid flow path of the device conduit 240.

Further in FIG. 2, the fitting coupler 200 comprises a contact pressure element 250, which is configured to sealingly press a conduit opening 260 to a mouth 270 where the device conduit 240 opens into the cavity 230. The conduit opening 260 represents an input into or an output out from a fluid flow path within the planar fluid conduit 210.

In the embodiment of FIG. 2, the contact pressure element 250 comprises a guidance 280 for receiving the planar fluid conduit 210 and for guiding it into the cavity 230 to the mouth 270, when the fitting coupler 200 together with the planar fluid conduit 210 is inserted into the cavity 230. In FIG. 2, the guidance 280 comprises a clearance 285 at a lateral side of a front piece 290 of the fitting coupler 200. In operation, a front side 295 of the front piece 290 presses in axial direction of the contact pressure element 250 towards a contact side 297 where the mouth 270 opens into the cavity 230. Accordingly, the planar fluid conduit 210 reaches through the clearance 285 and is bent over the front side 295, so that the conduit opening 260 faces towards the mouth 270. In operation, when the fitting coupler 200 has coupled the planar fluid conduit 210 with the fluidic device 220, the end of the planar fluid conduit 210 which is bent over the front side 295 is interposed between the front side 295 and the contact side 297, and the conduit opening 260 opens directly into the mouth 270.

The front piece 290 represents an axial force element to exert an axial force in an axial direction with respect to the cavity 230 or the contact pressure element 250 itself. The front piece 290 might be configured to exert the axial force as a spring-biased force. This can be achieved, for example, by providing one or more elastic elements, such as spring arranged in axial direction. Alternatively or in addition, the front piece 290 can be embodied itself to have elastic properties, for example by comprising sufficiently elastic materials. Alternatively, one or more of the components shown in FIG. 5A can be dimensioned to have enough elasticity to always keep the sealing force upright. It can be of great advantage to select the right material properties and form and manufacture the parts in the correct way to provide such elasticity properties.

Further in FIG. 2, the contact pressure element 250 comprises an external thread 298, which interacts with an internal thread 299 of the fluidic device 220. When and by screwing the contact pressure element 250 into the cavity 230, the front piece 290 exerts an axial force towards the contact surface 297 of the fluidic device 220 to sealingly couple the conduit opening 260 with the mouth 270.

Figure 3A:
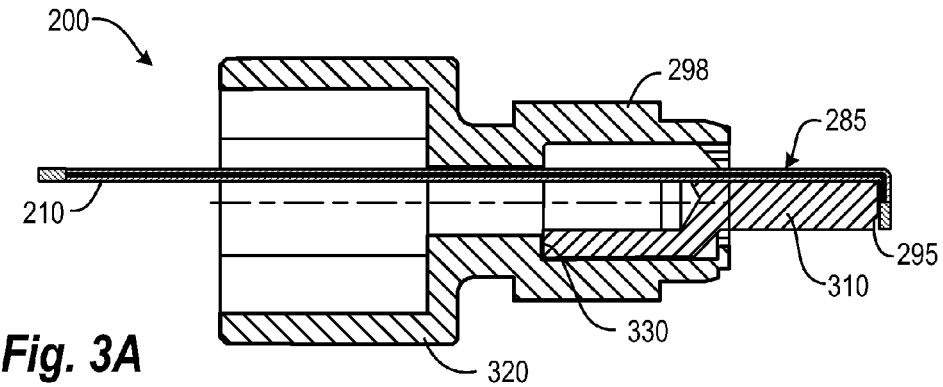
FIGS. 3A-3F illustrate another embodiment of the fitting coupler 200 as a two-piece device.
Figure 3B:
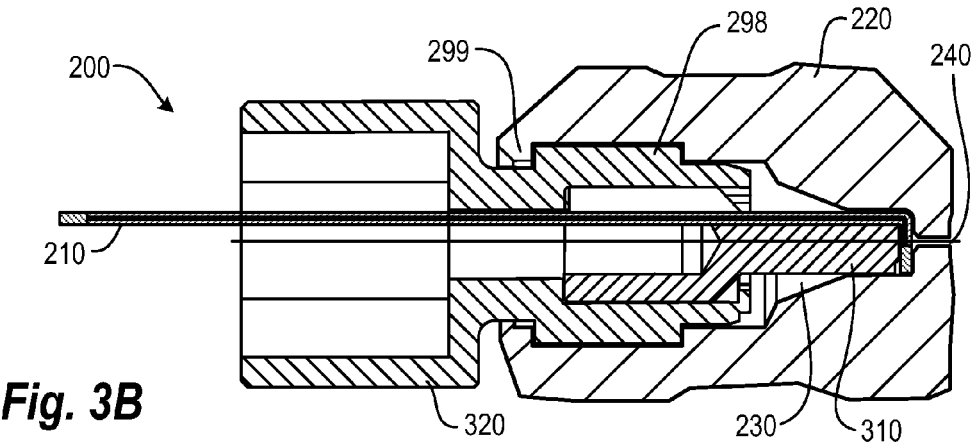
Figure 3C:
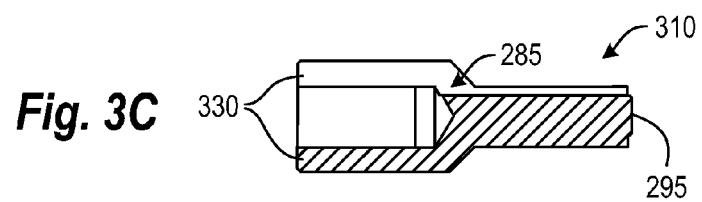
Figure 3D:
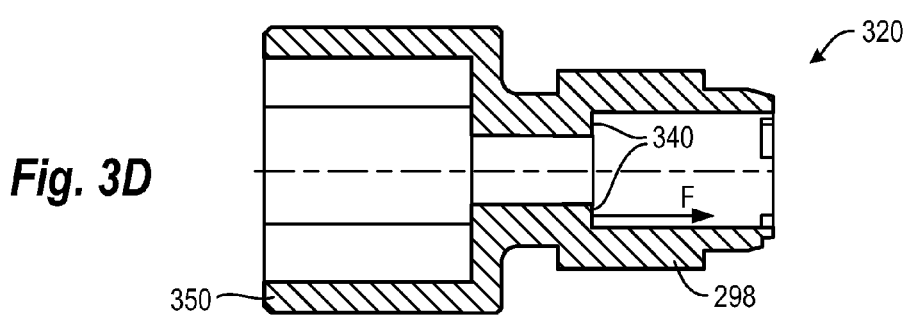
Figure 3E:
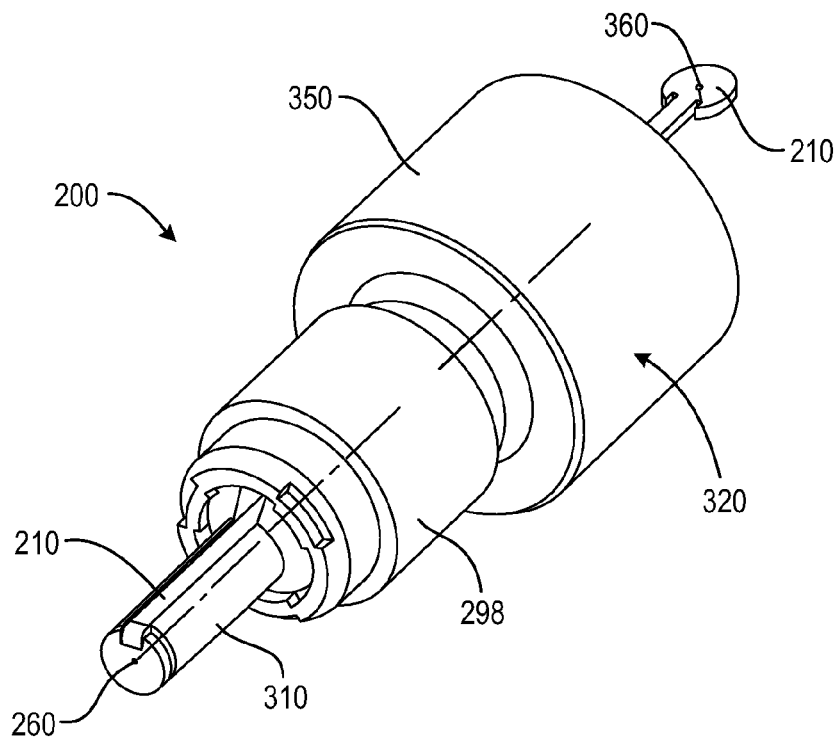

FIGS. 3A-3F illustrate another embodiment of the fitting coupler 200. In contrast to the embodiment of FIG. 2, the fitting coupler 200 is embodied as a two-piece device having a front element 310 and a rear element 320. FIG. 3A-3D and 3F show the fitting coupler 200 in cross sectional view, and FIG. 3E shows the fitting coupler 200 in three dimensional view. As in the embodiment FIG. 2, the planar fluid conduit 210 in the embodiment of FIG. 3 is guided in and by the clearance 285, so that the conduit opening 260 will face towards the mouth 270 when the fitting coupler is inserted into the cavity 230. In contrast to the embodiment of FIG. 2, the clearance 285 in the embodiments of FIG. 3 is only provided in the front element 310, so that only the front element 310 bears the planar fluid conduit, while the rear element 320 does not bear the planar fluid conduit 210 but only "loosely" leads it through its inside. In other words, the rear element 320 is fully decoupled from the planar fluid conduit 210 and can be rotated without in turn also rotating the planar fluid conduit 210, as will be explained further in detail, so that rotating the rear element 320 will not rotate the front element 310 and thus the planar fluid conduit 210 held thereby. This arrangement can ensure that the sealing surface will not suffer from tightening and may not be destroyed easily e.g. by handling of the operator.

Turning to FIG. 3A, the front element 310 comprises the front face 295. This can also be seen in FIG. 3C, which depicts the front element 310 only. The front element 310 further comprises a rear side 330 at an end opposing the front face 295. FIG. 3B corresponds to FIG. 3A but further shows the fitting coupler 200 inserted into the cavity 230 of the device 220.

FIG. 3D depicts the rear element 320 in isolated view. The rear element 320 has a shoulder 340 which, when the front element 310 and the rear element 320 are abutting with each other, abuts to the rear side 330 of the front element 310. The rear element 320 further comprises the external thread 298 and a handle 350 extending to a rear end of the rear element 320. The handle 350 can be used to turn/rotate the rear element 320. The handle can be formed of hexagon shape at outside or inside or other shapes like spanner flat. Else the surface can be roughened, a typical method is knurling. Another way to turn the screw 350 is to connect a tool to any of the aforementioned surfaces or flanges or connections with such functionality.

When the external thread 298 engages with the internal thread 299 of the fluidic device 220, the rotational movement of the rear element 320 will be converted in an axial force F. With the shoulder 340 abutting to rear side 330, the axial force F will be transmitted through the front element 310 and towards the front face 295 for sealingly coupling the planar fluid conduit 210 to the device 220 as explained above. A lubricant can be provided to reduce friction between the two parts 310 and 320, which may have a plated or coated surface.

FIG. 3E shows in three-dimensional representation the fitting coupler 200 as explained with respect to FIGS. 3A-3C. From FIG. 3E it can be seen well that the planar fluid conduit 210 in this embodiment extends along a lateral side of the front element 310 and bends over to the front face 295. The conduit opening 260 can be seen clearly in FIG. 3E. FIG. 3E also shows the other end of the planar fluid conduit 210, which also bears a second conduit opening 360. It goes without saying that the planar fluid conduit 210 is not limited to the embodiment shown in FIG. 3E but may e.g. be longer or having a different shaping. The centering of the opening 260 can be important for a proper function, and positioning of the planar structure 210 during assembly onto pin 310 should be provided carefully.

Figure 3F:
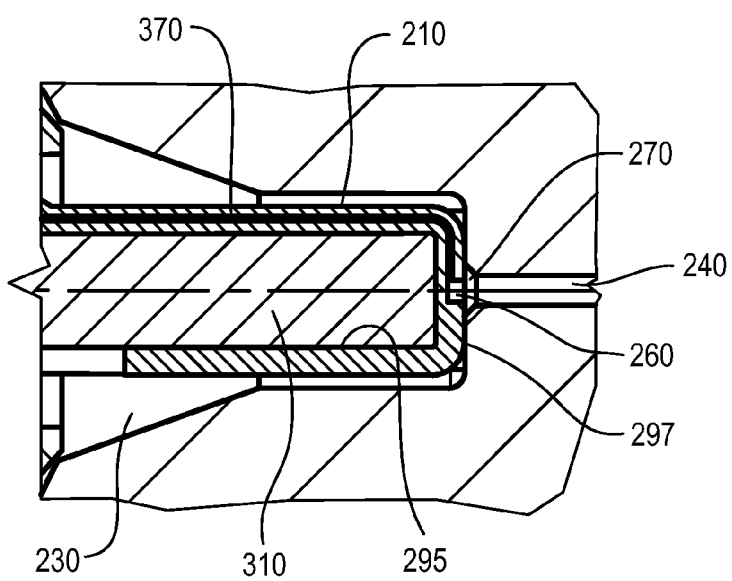

FIG. 3F shows an enlarged view of the right handed side of FIG. 3B, where the front element 310 presses against the contact face 297 of the fluidic device 220. The enlarged view of FIG. 3F schematically shows a flow path 370 within the planar fluid conduit 210, which extends between the conduit openings 260 and 360. The flow path 370 is provided by a conduit channel within the planar fluid conduit 210. The conduit channel 370 may have an essentially rectangular cross section as described in embodiments as cited in the introductory part of the description. As can be seen in FIG. 3F the conduit channel 370 extends to the conduit opening 260. As can also be seen in FIG. 3F, the conduit opening 260 directly extends to the mouth 270, thus directly coupling the flow path 370 of the planar fluid conduit 210 with the device conduit 240 of the fluidic device 220.

When disassembling the whole fitting coupler assembly, the screw 320 can pull out the possibly sticking front part without leaving any part into the cavity 220. Another advantage of the design can be that re-assembly of the fitting to the same port or another port can be repeated often without losing functionality. Another advantage of the design can be that the user can get feedback while tightening the connection, which helps to prevent over-loading of the parts. The feedback may consist in a sudden increase of force to tighten the connection which can give a clear feedback to the user who connects the parts.

Figure 4:
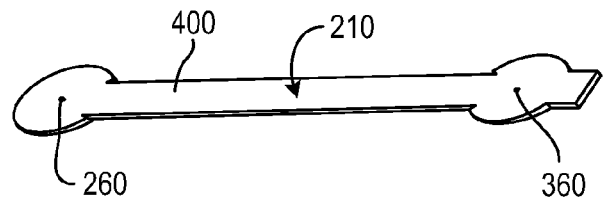
FIG. 4 shows in three-dimensional view an embodiment of the planar fluid conduit 210.

FIG. 4 shows in three-dimensional view an embodiment of the planar fluid conduit 210. The flow path of the conduit channel 370 connects the first conduit opening 260 and the second conduit opening 360. In the embodiment of FIG. 4, both conduit openings 260 and 360 open at a lateral side 400 of the planar conduit 210.

Figure 5A:
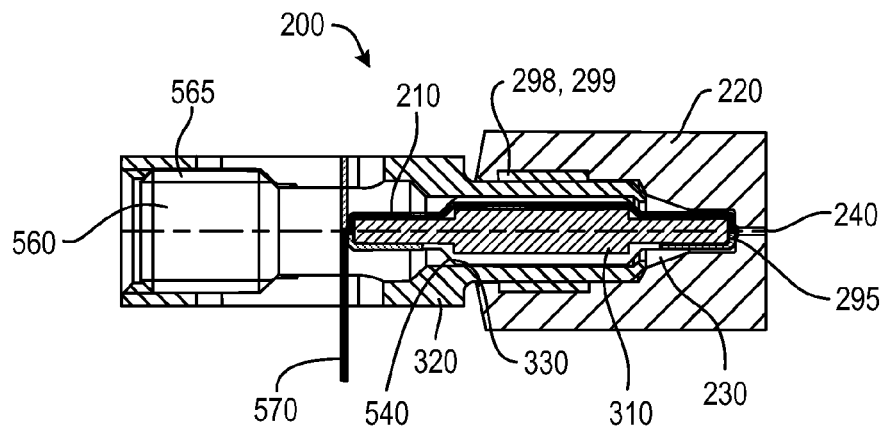
FIGS. 5A-5G illustrate a third embodiment according to the present invention.

FIGS. 5A-5G illustrate a third embodiment according to the present invention. FIG. 5A corresponds to the representation of FIGS. 2 and 3B. The fitting coupler 200 also comprises the front element 310 and the rear element 320. The front element 310 is embodied as a pin or pressure piece, and the rear element 320 is embodied as a housing. The fitting coupler 200 further comprises a screw 560, which can be better seen in FIG. 5E. In operation, the screw 560 interacts with a thread 565 of the rear element 320 housing the screw 560, thus pressing on a second planar fluid conduit 570, which again presses on the planar fluid conduit 210. This also fluidically couples the second planar fluid conduit 570 with the planar fluid conduit 210. It is clear that instead of the first and second planar conduits 210 and 570 being provided as individual parts, they may also be integrated in one conduit or the planar fluid conduit 210 may simply extend further. The embodiment of FIGS. 5, however, provides a modular structure which can be of advantage in certain applications.

The front element 310, here embodied as pin, transmits the pressing force from the screw 560 to the front face 295 to sealingly coupling the planar fluid conduit 210 with the device conduit 240.

The front element 310 is mechanically guided in the housing provided by the rear element 320, so that corresponding fluid openings will match and meet, as described above.

Figure 5B:
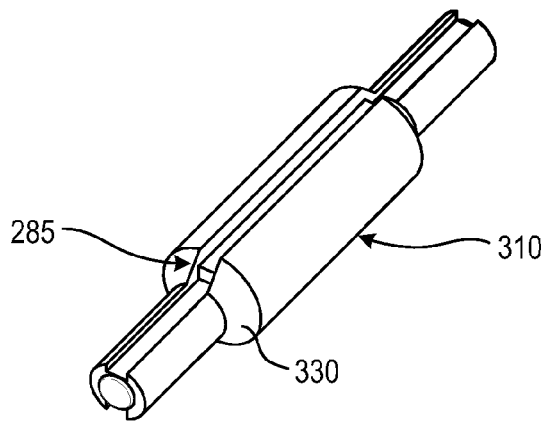
Figure 5C:
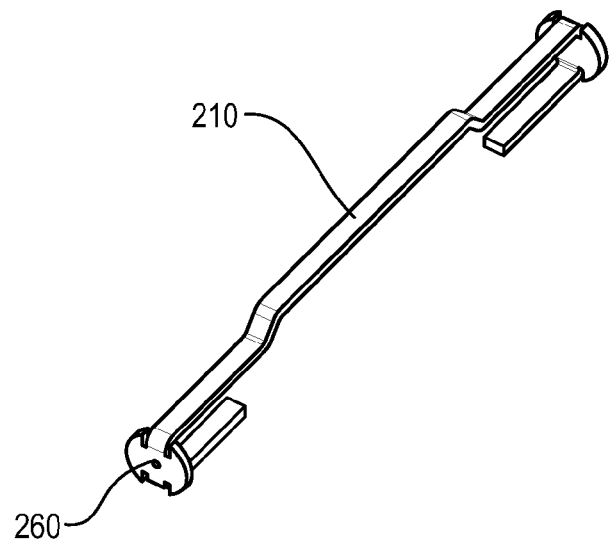
Figure 5D:
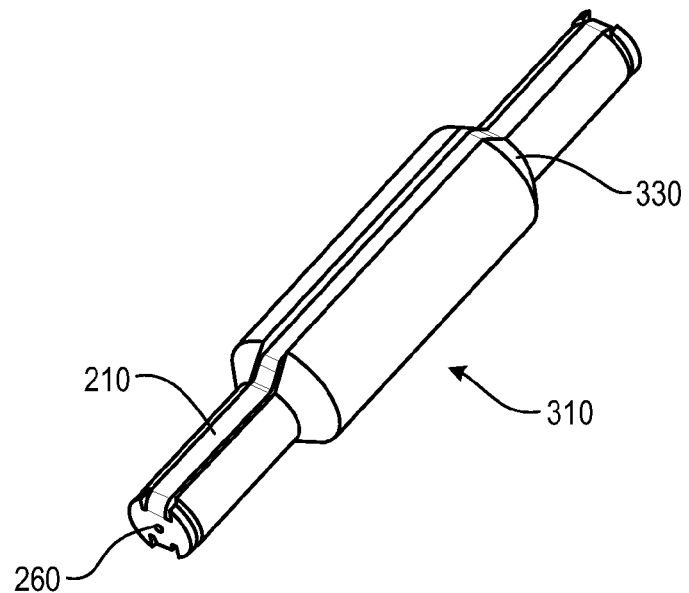

FIG. 5A shows the embodiment of the fitting coupler 200 in cross-sectional view. FIG. 5B shows the front element 310 in three dimensional view. FIG. 5C depicts the planar fluid conduit 210 in three dimensional view, and FIG. 5D shows the planar fluid conduit 210 assembled to the front element 310, also in three dimensional view.

Figure 5E:
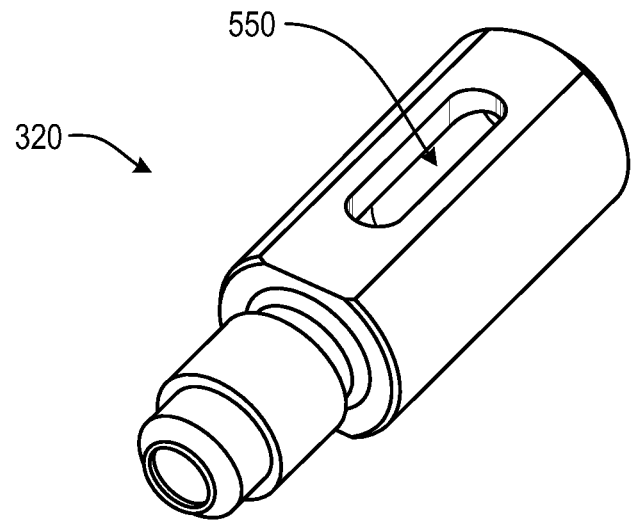

FIG. 5E shows in three-dimensional view the rear element 320. The rear element 320 acts as housing to guide the front element 310 with assembled fluidic channel 210. The second fluidic channel 570 can be assembled through an opening 550 to bring together the two planar fluid conduits 210 and 570 as shown in FIG. 5A. The screw 560 exerts pressure onto the two channels 210 and 570 to apply the contact pressure needed.

Figure 5F:
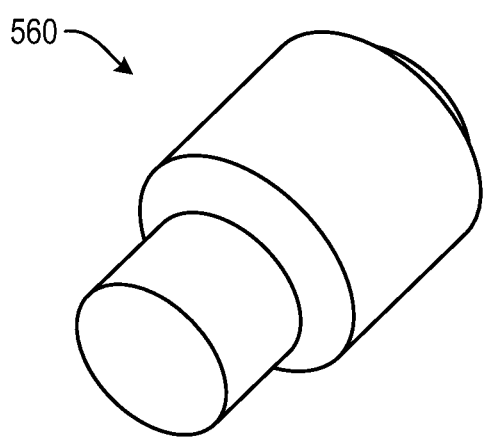

FIG. 5F shows in three-dimensional view the screw 560, which is used to couple the second planar fluid conduit 570 to the first planar fluid conduit 210 and which is located into the housing 320. The tread is not illustrated onto the bigger diameter. A tool holder recess at the back side may be provided to turn the screw 560. It can be, for example, of hexagon shape, for a splined shaft or another shape as required. Alternatively, a tool-less solution can be adapted if the screw 560 is replaced with a screw of another shape to be able to handle it manually without tools.

Figure 5G:
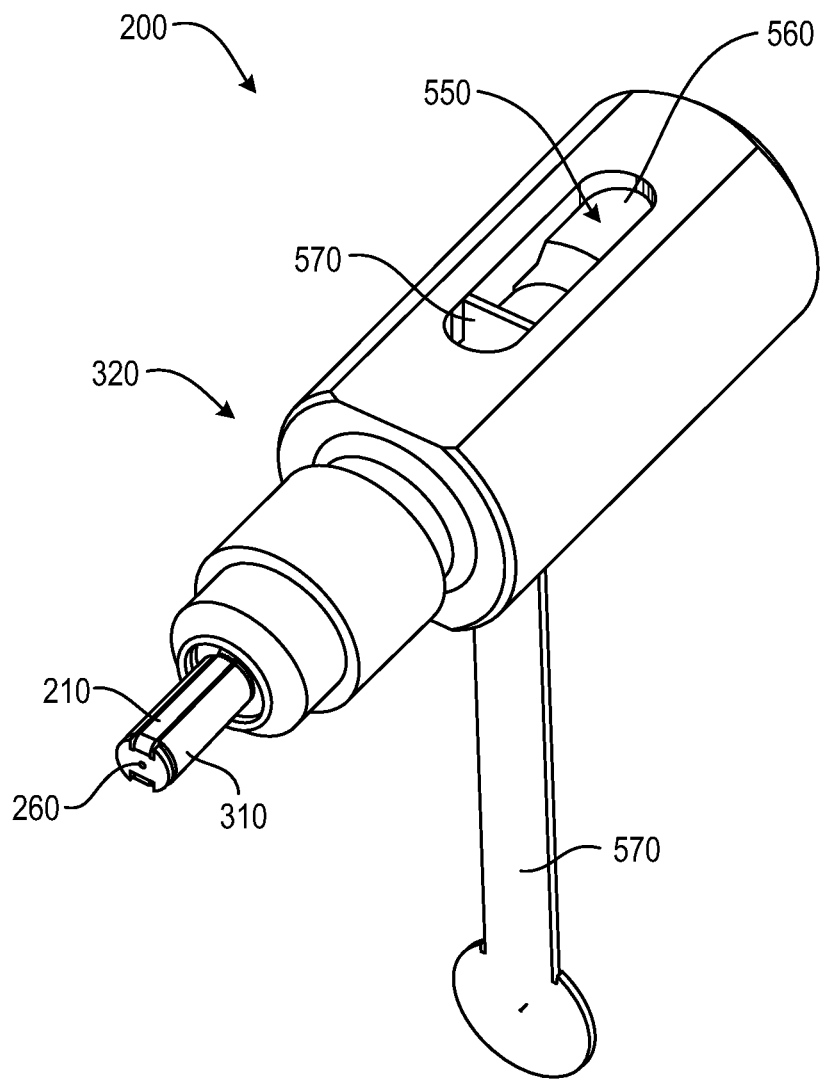

FIG. 5G shows in three-dimensional view the fully assembled fitting coupler 200 of the embodiment of FIG. 5. The assembly procedure can be designed to first screw in the housing 320 into the receiving port 220. Then pin 310 with assembled fluid channel 210 will be inserted into housing 320. Next the second fluid channel 570 will be inserted through one of the openings 550. Last the screw 560 will be inserted into housing 320 and compresses all parts to "close" the pressure-tight connection.

The invention claimed is:

1. A fitting coupler configured for coupling a planar fluid conduit and a fluidic device, wherein the fluidic device comprises a cavity, a device conduit, and a mouth where the device conduit opens into the cavity, the fitting coupler comprising:
   a contact pressure element configured for sealingly pressing the planar fluid conduit to the mouth, so that a conduit opening of the planar fluid conduit opens into the mouth; and
   a front face configured to abut against a contact side of the device conduit having the device opening, enabling the planar fluid conduit to be guided along a lateral side of the fitting coupler and bent over the front face, so that in use an end of the planar fluid conduit is interposed between the front face of the fitting coupler and the contact side of the device conduit.

2. The fitting coupler of claim 1, wherein the contact pressure element comprises an axial force element configured to exert an axial force in an axial direction with respect to the cavity.

3. The fitting coupler of claim 2, wherein at least one of:
   the axial force element provides a pressing force to sealingly press the planar fluid conduit to the mouth;
   the axial force element comprises a thread element configured to act together with a device thread element of the fluidic device to exert the axial force; or
   the axial force element is configured to exert the axial force as a spring-biased force.

4. The fitting coupler of claim 1, wherein the contact pressure element is configured for interacting with the cavity to sealingly press the planar fluid conduit to the mouth.

5. The fitting coupler of claim 4, wherein the contact pressure element is configured to interact with a surface of the cavity for sealingly pressing the conduit opening to the mouth.

6. The fitting coupler of claim 1, further comprising:
   a front element and a rear element,
   wherein the front element comprises the front face configured to abut against the contact side of the device conduit,
   the contact side comprises the mouth,
   a rear side of the front element is located at a side opposite to the front face,
   the rear element is configured to abut against the rear side of the front element and to exert an axial force on the front element in an axial direction with respect to the cavity.

7. The fitting coupler of claim 6, wherein at least one of:
   the front element and the rear element are embodied as individual parts but integrally coupled with each other;
   the front element and the rear element are configured to be detachable or removable from each other.

8. The fitting coupler of claim 6, wherein at least one of:
   one of the front element and the rear element is configured to be rotatable with respect to the other;
   one of the front element and the rear element is configured to be rotatable with respect to the fluidic device;
   one of the front element and the rear element is configured to be rotatable with respect to the other and also with respect to the fluidic device;
   the rear element is configured to be rotatable with respect to the front element;
   the rear element is configured to be rotatable with respect to the front element as well as with respect to the fluidic device;
   the rear element is configured to decouple the planar fluid conduit from a rotational movement of the rear element;
   the rear element comprises a thread element configured to act together with a device thread element of the fluidic device to exert a force on the rear side of the front element.

9. The fitting coupler of claim 1, wherein the planar fluid conduit has a conduit channel with an essentially rectangular shape; and the conduit opening at the end of the planar fluid conduit is in fluidic communication with the conduit channel.

10. The fitting coupler of claim 1, wherein the contact pressure element is configured to press the planar fluid conduit against the device, so that the conduit opening of the planar fluid conduit sealingly couples to the mouth of the device conduit.

11. A planar fluid conduit comprising:
   a conduit channel with an essentially rectangular shape, and
   a conduit opening at an end of the planar fluid conduit which is in fluidic communication with the conduit channel,
   wherein a fitting coupler, in accordance with claim 1, is coupled to the end of the planar fluid conduit and configured for coupling the conduit opening to a mouth in a cavity of the fluidic device.

12. A fitting comprising:
   a fluidic device having a cavity, a device conduit, and a mouth where the device conduit opens into the cavity,
   a planar fluid conduit having a conduit channel with an essentially rectangular shape, and a conduit opening at an end of the planar fluid conduit which is in fluidic communication with the conduit channel, and a fitting coupler, in accordance with claim 1, coupled to the end of the planar fluid conduit and being configured for coupling the conduit opening of the planar fluid conduit to the mouth.

13. A fluid separation system for separating compounds of a sample fluid in a mobile phase, the fluid separation system comprising:
- a mobile phase drive configured to drive the mobile phase through the fluid separation system;
- a separation unit configured for separating compounds of the sample fluid in the mobile phase, and
- a fitting coupler according to claim 1 for coupling a planar fluid conduit for conducting the mobile phase.

14. The fluid separation system of claim 13, further comprising at least one of:
- a sample injector configured to introduce the sample fluid into the mobile phase;
- a detector configured to detect separated compounds of the sample fluid;
- a collection unit configured to collect separated compounds of the sample fluid;
- a data processing unit configured to process data received from the fluid separation system;
- a degassing apparatus for degassing the mobile phase.

* * * * *